United States Patent [19]

Sher et al.

[11] Patent Number: 5,106,991

[45] Date of Patent: Apr. 21, 1992

[54] GEMINALLY SUBSTITUTED THIAHETEROCYCLIC CARBOXYLIC ACIDS AND DERIVATIVES THEREOF

[75] Inventors: Philip M. Sher, Plainsboro; Steven E. Hall, Ewing Township, Mercer County, both of N.J.

[73] Assignee: E. R. Squibb & Sons, Inc., Princeton, N.J.

[21] Appl. No.: 558,917

[22] Filed: Jul. 27, 1990

Related U.S. Application Data

[62] Division of Ser. No. 361,620, Jun. 2, 1989, Pat. No. 4,975,452.

[51] Int. Cl.$^5$ .................. C07D 275/00; A61K 31/425
[52] U.S. Cl. .................... 548/206; 548/213; 548/214
[58] Field of Search ............... 514/372; 548/206, 209, 548/214, 213

[56] References Cited

U.S. PATENT DOCUMENTS

| | | | |
|---|---|---|---|
| 4,258,058 | 3/1981 | Witte et al. | 425/309 |
| 4,443,477 | 4/1984 | Witte et al. | 424/319 |
| 4,752,613 | 7/1988 | Floyd et al. | 514/438 |
| 4,752,616 | 6/1988 | Hall et al. | 514/510 |
| 4,783,473 | 11/1988 | Hall et al. | 514/382 |
| 4,975,452 | 12/1990 | Sher et al. | 548/206 |

FOREIGN PATENT DOCUMENTS 194548A 9/1986 European Pat. Off. .

*Primary Examiner*—Nicholas S. Rizzo
*Attorney, Agent, or Firm*—Timothy J. Gaul

[57] ABSTRACT

Novel thromboxane receptor antagonists are disclosed, having the formula

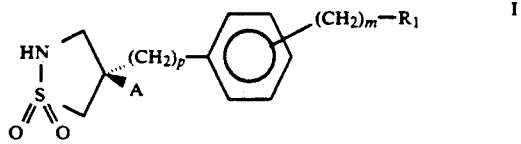

wherein:
A is aryl, optionally substituted with
  halogen,
  lower alkoxy,
  carboalkoxy,
  lower alkyl,
  alkylamino, or
  phenyl;
$R_1$ is COOH, COO—alkali metal (such as Na, K, or Li), COO—lower alkyl, $CONHSO_2R_2$, or 5-tetrazolyl;
$R_2$ is lower alkyl or aryl;
m is 0, 1, or 2; and
p is 2, 3, 4, or 5.

Also disclosed are novel intermediates of formula I compounds.

8 Claims, No Drawings

GEMINALLY SUBSTITUTED THIAHETEROCYCLIC CARBOXYLIC ACIDS AND DERIVATIVES THEREOF

CROSS-REFERENCE TO RELATED APPLICATION

This application is a divisional application from U.S. Ser. No. 361,620, filed Jun. 2, 1989, now U.S. Pat. No. 4,975,452.

FIELD OF THE INVENTION

The present invention relates to geminally substituted thiaheterocyclic carboxylic acids. These novel compounds are thromboxane receptor antagonists and therefore are useful in the treatment of thrombotic and vasospastic diseases.

BACKGROUND OF THE INVENTION

Thromboxane receptor antagonists and thrombocyte aggregation inhibitors useful in treatment of thrombotic disease are disclosed in the following patents:

(1) geminally substituted cyclic ether carboxylic acids (U.S. Pat. No. 4,783,473);
(2) sulfonamidothienylcarboxylic acids (U.S. Pat. No. 4,752,613);
(3) phenoxyalkyl carboxylic acid derivatives (U.S. Pat. No. 4,258,058);
(4) sulponamidophenylcarboxylic acids (U.S. Pat. No. 4,443,477);
(5) thioalkylphenylcarboxylic acids (U.S. Pat. No. 4,752,616); and
(6) sulfonamidoethyl compounds (European Patent No. 194,548A).

DETAILED DESCRIPTION OF THE INVENTION

Thromboxane Receptor Antagonists

It has now been discovered that compounds having the formula

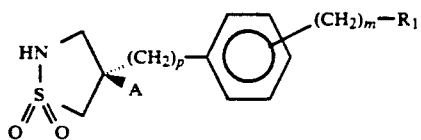

and the pharmaceutically acceptable salts thereof, including all stereoisomers thereof, are thromboxane receptor antagonists useful in treatment of thrombotic disease. In formula I and throughout this specification, the symbols above are as defined below.

A is aryl, optionally substituted with one or more of the following:
halogen;
lower alkyl;
carboalkyl;
lower alkoxy;
alkylamino; or
phenyl.

$R_1$ is COOH, COO— alkali metal (such as Na, K, or Li), COO— lower alkyl, CONHSO$_2$R$_2$, or 5-tetrazolyl.
$R_2$ is lower alkyl or aryl.
m is 0, 1 or 2.
p is 2, 3, 4 or 5.

Preferred are compounds in which $R_1$ is COOH, A is aryl or aryl substituted with halogen, p is 3, m is 1, and $(CH_2)_m—R_1$ is attached at the para position.

Definition of Terms

Listed below are definitions of various terms used to describe this invention. These definitions apply to the terms as they are used throughout the specification (unless they are otherwise limited in specific instances) either individually or as part of a larger group.

The term "lower alkyl" or "alkyl" as employed herein by itself or as part of another group includes both straight and branched chain hydrocarbon radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including one or two halo-substituents, such as F, Br, Cl or I or CF$_3$, an alkoxy substituent, an aryl substituent, an alkyl-aryl substituent, a haloaryl substituent, a cycloalkyl substituent or an alkylcycloalkyl substituent.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, 1 or 2 halogens (Cl, Br or F), and/or 1 or 2 lower alkoxy groups.

The term "aralkyl", "aryl-alkyl" or "aryl-lower alkyl" as used herein by itself or as part of another group refers to lower alkyl groups as discussed above having an aryl substituent, such as benzyl.

The terms "lower alkoxy" or "alkoxy" refer to an alkyl group linked to an oxygen atom.

The term "alkylamino" refers to an alkyl group linked to —NH—.

The term "alkylsulfonyl" refers to an alkyl group linked to —SO$_2$—.

The term "arylsulfonyl" refers to an aryl group linked to —SO$_2$—.

The term "aralkylsulfonyl" refers to an aralkyl group linked to —SO$_2$—.

The term "alkoxycarbonyl" refers to an alkoxy group linked to —C(=O)—.

The terms "halogen" or "halo" or "halide" as used herein by themselves or as part of another group refers to chlorine, bromine, fluorine, iodine or CF$_3$, with chlorine being preferred.

The terms "(CH$_2$)$_m$" and "(CH$_2$)$_p$" where present include a straight or branched chain radical having the above specified number of carbons in the normal chain and may contain one or more lower alkyl and/or lower alkoxy substituents. Examples of (CH$_2$)$_m$ and (CH$_2$)$_p$ groups include —CH$_2$—,

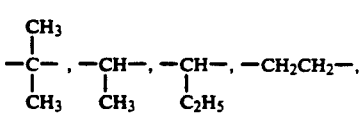

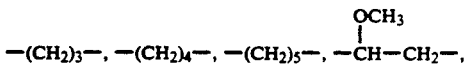

-continued $-\overset{CH_3}{\underset{}{CH}}-CH_2-$, $-CH_2-\overset{OCH_3}{\underset{H}{C}}-$, $-\overset{CH_3}{\underset{CH_3}{C}}-CH_2-$, $-(CH_2)_5-$, $-\overset{CH_3}{\underset{}{CH}}-$, $-(CH_2)_2-\overset{CH_3}{\underset{}{CH}}-$, $-CH_2-\overset{CH_3}{\underset{CH_3}{CH}}-$, $-(CH_2)_2-\overset{CH_3}{\underset{CH_3}{C}}-$, $-CH_2-\overset{CH_3}{\underset{}{CH}}-\overset{CH_3}{\underset{}{CH}}-CH_2-$, $-CH_2-\overset{}{\underset{CH_3}{CH}}-CH_2-\overset{}{\underset{CH_3}{CH}}-$ the like. The $(CH_2)_m-R_1$ group may be attached at the ortho, meta, or para position, with the para position preferred.

In accordance with the above symbols and definitions, compounds of formula I include the following exemplary compound:

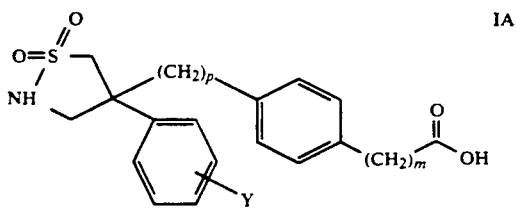

IA wherein Y may be hydrogen or halogen.

Methods of Preparation

Formula I compounds may be prepared by the exemplary process as outlined below. Two exemplary methods of preparation are described.

Preparation may begin with a bromophenyl alkanoic acid. This compound may undergo:

(a) reduction, wherein it is treated with a borane such as $BH_3 \cdot$ tetrahydrofuran to form the reduced compound

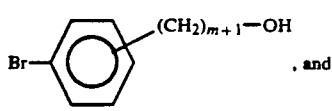

II

, and (b) monosilylation, wherein it is treated with a protecting compound such as thexyl dimethyl silyl chloride, t-butyl dimethyl silyl chloride, or t-butyl diphenyl silyl chloride to form the protected compound

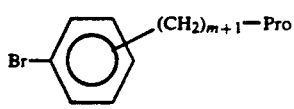

III wherein Pro represents a protected alcohol group, such as

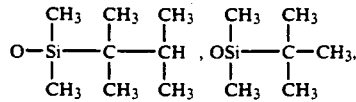

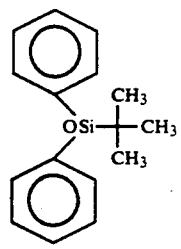

and the like.

Compound III may be converted to a Grignard reagent by treatment with magnesium, and the Grignard reagent may be mixed with a compound having the formula $Br-(CH_2)_p-Br$   III' wherein p is 3, 4 or 5. (Compound IV wherein p is 2 can be prepared as described in U.S. Pat. No. 4,752,616.) In a copper-catalyzed coupling reaction, under an inert atmosphere at 0° C. in an organic solvent, compounds III and III' may form the compound

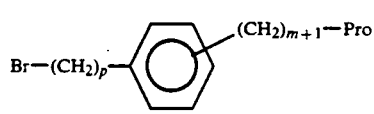

IV

Compound IV may react with an iodide (e.g., NaI) in an organic solvent at room temperature, undergoing a halide exchange to form the iodide compound

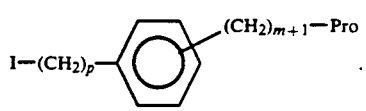

V

Compound V may be mixed with a compound having the formula $A-CH_2-CN$   V'.

Compound V may be mixed with a pre-formed mixture of compound V' and a base (e.g., lithium bis(trimethylsilyl)amide) at −78° C. under an inert atmosphere in an organic solvent and allowed to warm to room temperature to yield a compound having the formula

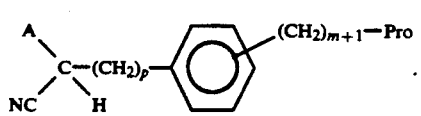

VI

The nitrile compound of formula VI may then be further alkylated to form a nitrile-alcohol. Compound VI may be mixed first with a base (e.g., lithium bis(trimethylsilyl)amide) and then paraformaldehyde under an inert atmosphere at −78° C. in an organic solvent, to form a compound having the formula

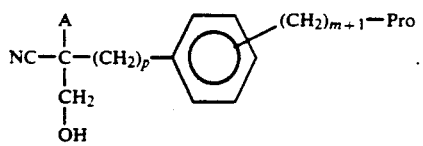

Compound VII may be reduced to an aminoalcohol by mixing it with a reducing agent (e.g., lithium aluminum hydride) in ether. under an inert atmosphere at 0° C. When this mixture is allowed to warm to room temperature, the result is a compound having the formula

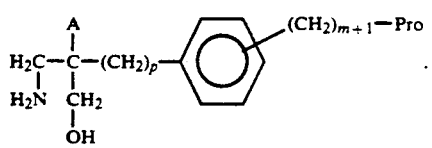

Compound VIII may be mixed with a nitrogen-protecting compound, such as di-t-butyl dicarbonate, under an inert atmosphere at room temperature, to form a compound having the formula

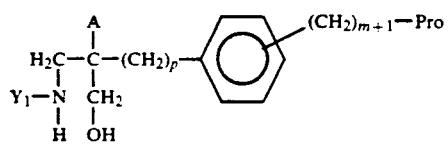

wherein $Y_1$ is a nitrogen-protecting group, such as t-butyloxycarbonyl.

Compound IX may be sulfonated under an inert atmosphere at $-25°$ C., by mixing compound IX with an alkyl- or arylsulfonylhalide in the presence of a base and warming to room temperature to form a compound of the formula

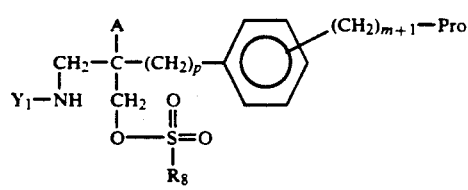

wherein $R_8$ is alkyl or aryl.

Compound X may be mixed with an alkali metal thioacetate (e.g., potassium thioacetate) under an inert atmosphere in an organic solvent (e.g., dimethylsulfoxide), resulting in a compound having the formula

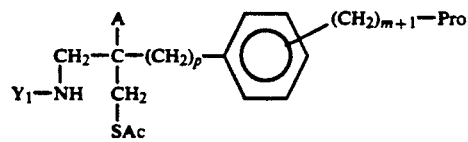

wherein Ac is acetyl.

Compound XI may be treated with an oxidizing agent in an organic solvent and left to stand for 12 to 72 hours at 0° C. to 60° C. The result is a mixture of compounds of the formulas

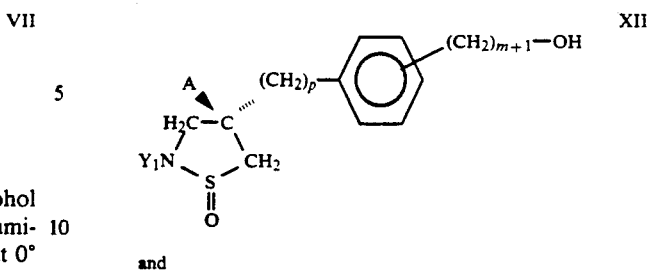

and

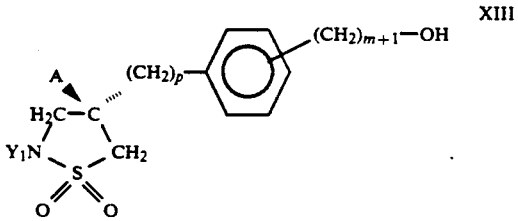

This oxidative cyclization was an unexpected result, especially because of the presence of the $Y_1$ nitrogen-protecting group. This process is believed to be novel and useful in producing thromboxane receptor antagonists. The process does not depend on the presence of the A, $(CH_2)_p$, $(CH_2)_m$, aryl, or Pro groups and is applicable to compounds having aryl, alkyl, hydroxyaryl, and hydroxyalkyl substituents instead of those groups. The preferred oxidizing agent is a buffered mixture of alkali-hydrogen persulfate, such as "Oxone"® (2 $KHSO_5 \cdot KHSO_4 \cdot K_2SO_4$).

Compound XII may be converted to compound XIII by adding an oxidizing reagent (e.g. m-chloroperbenzoic acid) and sodium bicarbonate at room temperature in a mixture of water and an organic solvent.

Compound XIII may be oxidized by mixing it with Jones reagent at 0° C. under an inert atmosphere. The resulting compound follows the formula

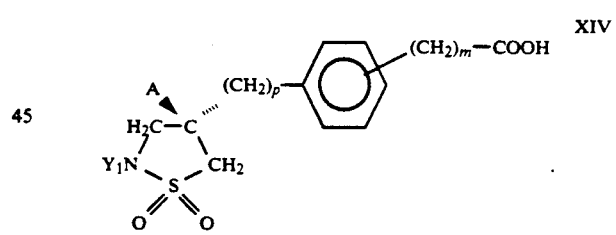

The nitrogen-protecting group ("$Y_1$") may be removed when compound XIV is mixed with trifluoroacetic acid, resulting in a compound following formula IA. Other formula I compounds can be prepared by treatment with an alkali metal hydroxide, such as sodium hydroxide or potassium hydroxide.

Preparation of formula I compounds led to the discovery of several novel and useful intermediate compounds. Specifically, compounds VI through XIV above are novel and useful and form an integral part of this invention.

Utility of Compounds

The compounds of this invention are thromboxane receptor antagonists (or intermediates thereof) and as such are useful as inhibitors (or intermediates thereof) in thromboxane receptor mediated actions. The term "thromboxane receptor antagonist" includes compounds which are so-called thromboxane A₂ receptor antagonists, thromboxane A₂ antagonists, thromboxane A₂/prostaglandin endoperoxide antagonists, TP-receptor antagonists, or thromboxane antagonists.

The compounds of this invention are useful as inhibitors of platelet function —— i.e. for the prevention and treatment of thrombotic vascular occlusive disorders, whether complete or partial, including:
(1) arterial thrombosis, including that of the coronary, cerebral, ophthalmic, hepatic, mesenteric, renal, peripheral arteries or vascular or organ grafts,
(2) unstable angina,
(3) transient ischemic attacks, and
(4) intermittent claudication.

They may also be useful to prevent thrombosis following vascular injury produced in the course of such diagnostic and therapeutic procedures as endarterectomy and angiography. The compounds may be useful in treatment or prevention of disorders characterized by platelet consumption and/or activation, including platelet activation, dysfunction, and/or loss resulting from:
(1) extracorporeal circulation,
(2) use of radiographic contrast agents,
(3) thrombotic thrombocytopenia purpura,
(4) disseminated intravascular coagulation,
(5) purpura fulminans,
(6) hemolytic transfusion reaction, or
(7) hemolytic uremic syndrome.

The compounds may also be used in treatment of venous thrombosis or embolism, including pulmonary embolism, deep venous thrombosis, hepatic vein thrombosis, and renal vein thrombosis.

The compounds of this invention are also useful as inhibitors of arterial or venous vasoconstriction. Accordingly, they may be useful to prevent vasoconstriction associated with:
(1) unstable angina,
(2) chronic stable angina,
(3) variant (Prinzmetal's) angina,
(4) Raynaud's syndrome,
(5) migraine headache,
(6) vasospasm of the coronary, cerebral, ophthalmic, hepatic, mesenteric, renal, or peripheral arteries,
(7) vascular grafts,
(8) vascular injury, such as that associated with surgery or trauma,
(9) hypertension of pregnancy,
(10) hepato-renal syndrome, and
(11) pulmonary hypertension.

The compounds of this invention are useful as inhibitors of bronchoconstriction, i.e., airway hyperresponsiveness, allergic bronchospasm, asthma, and bronchoconstrictive responses to environmental, infectious, noxious or mechanical stimuli.

The compounds of this invention are useful as inhibitors of ischemic and reperfusion injury to various tissues —— including the myocardium, skin, brain, bowel, or kidney —— alone or in combination with other agents intended to restore blood flow. For example, these compounds may be useful for improving postischemic myocardial function and decreasing myocardial infarct size. These compounds may benefit persons with ischemia caused by reduced blood flow during diagnostic or therapeutic procedures; for example, they may reduce the myocardial stunning observed after bypass surgery. In addition, they may be useful for reducing tissue injury caused by stroke.

In addition, the thromboxane receptor antagonists of the invention may be used with a thrombolytic agent such as t-PA, streptokinase, urokinase, prourokinase or anisoylated plasminogenstreptokinase activator complex (APSAC) within 6 hours of a myocardial infarction. In such case, the thrombolytic agent may be used in amounts conventionally employed, for example, as disclosed in the Physicians' Desk Reference for reducing post-ischemic myocardial injury.

The compounds of this invention may be useful in prevention or treatment of other conditions, including burns, diabetic retinopathy, and tardive dyskinesia. The compounds may be useful in potentiating diuretic-induced diuresis.

The compounds of this invention may also be used in combination with a cyclic AMP phosphodiesterase (PDE) inhibitor, such as theophylline or papaverine, in the preparation and storage of platelet concentrates.

Method of Use

The compounds of formula I can be administered orally or parenterally to various mammalian species known to be subject to such maladies (e.g., humans, cats, dogs and the like). An effective dosage is about 1 to 100 mg/kg, preferably about 1 to 50 mg/kg, and especially about 2 to 25 mg/kg. Single or 2 to 4 divided daily doses are preferred.

The active substance can be utilized as a tablet, capsule, solution or suspension containing about 5 to about 500 mg per unit of dosage of a compound or mixture of compounds of formula I. They may be compounded in conventional manner with a physiologically acceptable vehicle or carrier, excipient, binder, preservative, stabilizer, flavor, etc., as called for by accepted pharmaceutical practice.

The compounds of formula I may also be administered topically to treat peripheral vascular diseases and as such may be formulated as a cream or ointment.

Preferred Embodiments

The following examples represent preferred embodiments of the present invention. Unless otherwise indicated, all temperatures are expressed in degrees Centigrade.

Example 1

4-[3-(4-Phenyl-4-isothiazolidinyl)propyl]benzene-acetic acid,S,S-dioxide.

A.

1-Bromo-4-[2-[[dimethyl(1,1,2-trimethylpropyl)silyl]oxy]-ethyl]benzene

This intermediate (hereinafter "intermediate A") was prepared in two steps. 4-Bromophenylacetic acid underwent diborane (B₂H₆) reduction. A solution of the resulting alcohol then underwent silylation with sodium hydride (NaH) and thexyl dimethyl silyl chloride.

B.

1-(3-Bromopropyl)-4-[2-[[dimethyl(1,1,2-trimethylpropyl)silyl]oxy]ethyl]benzene

Preparation of intermediate B began by, under argon, combining:
(1) 7.00 g (0.29 mol) of magnesium,
(2) one crystal of iodine; and
(3) 70 ml of dry tetrahydrofuran.

Ten percent of a solution containing 50 g (0.14 mol) of intermediate A in 10 ml of dry tetrahydrofuran was added to the above mixture while it was stirred under argon at 30° C. This mixture was stirred vigorously, and the iodine color disappeared in five minutes. The remainder of the solution was added dropwise over fifteen minutes. This mixture was heated at 40° C for an hour and cooled to room temperature.

A second solution was brought in at this point, containing:
(1) 18 ml (0.18 mol) of 1,3-dibromopropane;
(2) 28 ml (2.8 mmol) of 0.1 M dilithium tetrachlorocuprate ($Li_2CuCl_4$) in tetrahydrofuran; and
(3) 50 ml of dry tetrahydrofuran.

While the second solution was stirred, the above mixture was added to it at such a rate (70 minutes) that the temperature of the resulting mixture did not exceed 7° C. (An additional 100 ml was added to rinse in the residue of the above mixture).

The latter reaction mixture was stirred first at 0° C. for one hour, then at room temperature for two hours. The reaction mixture was cooled to 0° C. and quenched by adding 30 ml of methanol dropwise for over 5 minutes. The mixture was concentrated in vacuo and partitioned between saturated ammonium chloride solution (800 ml) and ether (3×800 ml). The combined ether extracts were dried with magnesium sulfate, filtered and concentrated in vacuo. The crude produce was subjected to bulb-to-bulb distillation under vacuum to give 37.8 g (a 68% yield) of intermediate B.

C.
1-[2-[[Dimethyl(1,1,2-trimethylpropyl)silyl]oxy]ethyl]-4-(3-iodopropyl)benzene Preparation of intermediate C began with a somewhat impure solution of intermediate B (9.3 g, less than 24 mmol) in 30 ml of acetone. The acetone solution first had been dried by stirring over $K_2CO_3$. 0.1 g sodium bicarbonate and 19.7 g sodium iodide (131 mmol) was then added to the solution.

The mixture was stirred in the dark at room temperature overnight. Water and 3 M aqueous sodium bisulfite solution was added, and the mixture was extracted with dichloromethane three times. The combined extracts were dried over sodium sulfate and evaporated. Trace moisture was removed azeotropically by rotoevaporation first with toluene (twice), then hexane (twice). Exposure to high vacuum gave 10.2 g (a 97% yield) of the somewhat impure intermediate C.

D.
α-[3-[4-[2-[[Dimethyl(1,1,2-trimethylpropyl)silyl]oxy]ethyl]phenyl]propyl]benzeneacetonit rile Preparation of intermediate D used three solutions. The first was 1.29 g (11.0 mmmol) of phenylacetonitrile in 20 ml of dry tetrahydrofuran; the second, 13.2 ml (13.2 mmol, 1.2 eq) of 1 M lithium bis(trimethylsilyl)amide in tetrahydrofuran; the third, 5.0 g (11.6 mmol, 1.05 eq) of intermediate C in 10 ml of dry tetrahydrofuran.

The second solution was added dropwise to the first while the first was stirred at −78° under argon. After an hour of stirring, the third solution was added dropwise. After stirring the mixture of all three solutions for an hour in the dark, the mixture was allowed to warm slowly to room temperature. Stirring continued for three days at room temperature.

1 ml of saturated ammonium chloride solution was then added, causing precipitation. The precipitate was filtered off, washed with tetrahydrofuran, and concentrated. The concentration residue was flash-chromatographed with zero to three percent ethyl acetate in hexanes gradient. In result, 1.91 g of 50% pure and 1.75 g of 100% pure intermediate D appeared, for a total yield of approximately 60%.

E.
α[3-[4-[2-[[Dimethyl(1,1,2-trimethylpropyl)silyl]oxy]ethyl]phenyl]propyl]-α(hydroxymet hyl)benzeneacetonitrile Preparation of intermediate E began with two solutions. The first was 1.12 g (2.67 mmol) of intermediate D in 15 ml of dry tetrahydrofuran; the second, 5.0 ml (5.0 mmol, 1.9 eq) of 1.0 M lithium bis(trimethylsilyl)amide in tetrahydrofuran.

The second solution was added dropwise to the first, which was stirred under argon at −78° C. After an hour of stirring, 500 mg (16.7 mmol) of solid paraformaldehyde was added. After 30 minutes of continued stirring at −78° C., the mixture was allowed to warm slowly to 0°. Stirring continued at 0° for forty-five minutes.

The mixture precipitated with addition of aqueous ammonium chloride solution. The precipitate was filtered, washing with ethyl acetate, and the filtrate was concentrated. The residue was flash-chromatographed in a 15 to 30 percent solution of ethyl acetate in hexanes, yielding 870 mg of pure intermediate E as an oil. The yield was 72%.

F.
2-(Aminomethyl)-2-phenyl-5-[4-[2-[[dimethyl(1,1,2-trimethylpropyl)silyl]oxy]ethyl]benz ene]pentanol Preparation of intermediate F employed:
(1) 870 mg (1.93 mmol) of intermediate E in 20 ml of dry ether, and
(2) 280 mg (7.4 mmol, 3.8 eq) of lithium aluminum hydride.

These two were mixed under argon at 0° C., then stirred for 30 minutes at room temperature.

Next, the mixture was recooled to 0° C., mixed with 20% ethyl acetate in ethyl ether to quench the hydride, and rewarmed to room temperature. While it was stirred vigorously, the mixture was diluted with, in sequence, 0.25 ml of water, 0.25 ml of 15% aqueous sodium hydroxide solution, and 0.75 ml of water.

The resulting mixture was filtered, the filter cake washed with a 10 percent solution of (10% concentrated aqueous ammonia/methanol) in ethyl ether, and the filtrate evaporated. The residue was rotoevaporated with dichloromethane and exposed to high vacuum, resulting in an oil residue weighing 1.09 g. The oil was impure intermediate F.

G.
[5-[4-[2-[[Dimethyl(1,1,2-trimethylpropyl)silyl]oxy]ethyl]phenyl]-2-(hydroxymethyl)-2-phenylpentyl]carbamic acid, 1,1-dimethylethyl ester For intermediate G, the oil residue from part F was mixed with 1.0 g (4.6 mmol) of di-t-butyl dicarbonate in 15 ml of dichloromethane. This mixture was stirred under argon at room temperature for thirty minutes, after which the solvent was evaporated. The mixture was flashchromatographed with a 15 to 60 percent solution of ethyl acetate in hexanes. The result was an oil weighing 530 mg (a 49% yield from intermediate E).

H.
[5-[4-[2-[[Dimethyl(1,1,2-trimethylpropyl)silyl]oxy]ethyl]phenyl]-2-[[(methylsulfonyl)oxy]methyl]-2-phenylpentyl]carbamic acid, 1,1-dimethylethyl ester Preparation of intermediate H employed:
(1) 530 mg (0.95 mmol) of intermediate G in 10 ml of dichloromethane,
(2) 144 mg (1.43 mmol, 1.5 eq) of triethylamine, and
(3) 120 mg (1.05 mmol, 1.1 eq) of methanesulphonyl chloride.

The latter was added dropwise to the former two while they were stirred together under argon at −25° C. Added thereafter was an additional 0.3 eq of methanesulphonyl chloride and, after warming to room temperature, water.

The mixture was then extracted twice with dichloromethane, and the extracts were dried over sodium sulfate and evaporated. Flash chromatography (with 15 to 25% ethyl acetate in hexanes) gave 510 mg of intermediate H as an oil. Its yield wa 85%.

I.
[2-[(Acetylthio)methyl]-5-[4-[2-[[dimethyl(1,1,2-trimethylpropyl)silyl]oxy]ethyl]phenyl]-2-phenylpentyl]carbamic acid, 1,1-dimethylethyl ester Preparation of intermediate I began with 510 mg (0.8 mmol) of intermediate H in 15 ml of dry tetrahydrofuran under argon. Added to this solution were:
(1) 184 mg (1.61 mmol, 2.0 eq) of potassium thioacetate, and
(2) 1 ml of dimethylsulfoxide.

The mixture was heated to reflux, so that the potassium thioacetate dissolved, the solution browned, and a precipitate formed. Several more aliquots of potassium thioacetate and dimethylsulfoxide were added over five more days of refluxing.

After five days, the mixture was cooled, diluted with water, and extracted with dichloromethane three times. The extracts were combined, dried over sodium sulfate and evaporated. The resulting oil was heated under vacuum to remove residual dimethylsulfoxide. Flash chromatography (with 5 to 15% ethyl acetate in hexanes) gave 380 mg of 90% pure intermediate I. Its yield was 70%.

J.
4-[3-[4-(2-Hydroxyethyl)phenyl]propyl]-4-phenyl-2-isothiazolidinecarboxylic acid, 1,1-dimethylethyl ester, S-oxide Preparation of intermediate J employed two solutions:
(1) 380 mg (0.55 mmol) of the 90% pure intermediate J in 6 ml of methanol and 10 ml of tetrahydrofuran, and
(2) 8 ml (1.5 mmol, 2.7 eq) of 0.2 M aqueous "Oxone" ® solution.

These solutions were stirred together at room temperature and formed a precipitate immediately. Stirring continued for three days, during which thin layer chromatography detected several transient intermediates.

Finally, the mixture was diluted with water and extracted three times with ethyl acetate. The extracts were dried over sodium sulfate and evaporated. Flash chromatography (with 10 to 100% ethyl acetate in hexanes) gave (1) 60 mg of pure intermediate J as a mixture of diastereomers and
(2) 60 mg of pure intermediate K (see below).
Intermediate J was formed in 25% yield; intermediate K, 24%.

K.
4-[3-[4-(2-Hydroxyethyl)phenyl]propyl]-4-phenyl-2-isothiazolidinecarboxylic acid, 1,1-dimethylethyl ester, S,S-dioxide Intermediate I was dissolved in dichloromethane and treated with an excess of m-chloroperbenzoic acid at room temperature. The excess m-chloroperbenzoic acid was then quenched with dimethylsulfide.

Saturated aqueous sodium bicarbonate was then added. The mixture was extracted several times with ethyl ether, the extracts dried over sodium sulfate, and the solvent evaporated. The result was the intermediate K in crude form.

L.
4-[3-[2-[(1,1-Dimethylethoxy)carbonyl]-4-phenyl-4-isothiazolidinyl]propyl]benzeneacetic acid, S,S-dioxide Preparation of intermediate L began with the pure intermediate K from Part J and the crude intermediate K from part K, both placed in 25 ml of acetone under argon at 0°. 2 ml of Jones reagent was added, and the mixture was stirred for thirty minutes. Still at 0° C., the mixture then received in sequence 2-propanol (to quench excess reagent), 3 M aqueous sodium bisulfite solution, and brine.

Extraction (three times) with ethyl acetate followed. The extracts were dried over sodium sulfate, and the solvent was evaporated. Flash chromatography followed, using a 20 to 40 percent solution of (5% acetic acid/ethyl acetate) in hexanes gradient. Thereafter, the acetic acid was azeotropically removed by (1) repeated retoevaporation with chloroform and toluene and (2) exposure to high vacuum.

The yield was 110 mg of pure intermediate L as an oil.

M. Example 1

In this final step, 2 ml of trifluoroacetic acid was mixed with 110 mg (0.23 mmol) of intermediate L in 6 ml of dichloromethane. This mixture was stirred for an hour at room temperature.

Thereafter, the dichloromethane was evaporated and the trifluoroacetic acid azeotropically removed by rotoevaporation with chloroform. Exposure to high vacuum gave a pure, solid sample of Example 2.

The foregoing example represents a preferred embodiment of the invention. Other embodiments are possible, as will be understood by those skilled in the art. This example is meant to be illustrative rather than limiting.

What is claimed is:
1. A compound represented by the formula

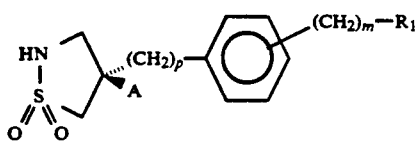

and pharmaceutically acceptable salts thereof, and all stereoisomers thereof, wherein:

A is aryl, optionally substituted with one or more of
- halogen,
- lower alkoxy,
- carboalkoxy,
- lower alkyl,
- alkylamino, or
- phenyl;

$R_1$ is COOH, COO—alkali metal, COO—lower alkyl, $CONHSO_2R_2$, or 5-tetrazolyl;

$R_2$ is lower alkyl or aryl;

m is 0, 1, or 2; and p is 2, 3, 4 or 5;

and wherein "aryl" refers to monocyclic and bicyclic aromatic groups having from 6 to 10 carbon atoms in the ring portion.

2. The compound of claim 1 wherein $R_1$ is COOH.

3. The compound of claim 1 wherein A is aryl substituted with halogen.

4. The compound of claim 1 wherein A is phenyl.

5. The compound of claim 1 wherein p is 3.

6. The compound of claim 1 wherein m is 1.

7. The compound of claim 1, wherein —$(CH_2)_m$—$R_1$ is attached at a para position.

8. The compound according to claim 1, 4-[3-(4-phenyl-4-isothiazolidinyl)propyl]benzeneactetic acid, S,S-dioxide.

* * * * *